United States Patent
Beavin

Patent Number: 5,273,038
Date of Patent: Dec. 28, 1993

[54] COMPUTER SIMULATION OF LIVE ORGAN

[76] Inventor: William C. Beavin, 609 Clara Ave. Apt. #9, St. Louis, Mo. 63112

[21] Appl. No.: 801,914

[22] Filed: Dec. 3, 1991

Related U.S. Application Data

[63] Continuation-in-part of Ser. No. 550,343, Jul. 9, 1990, abandoned.

[51] Int. Cl.$^5$ ............................................. A61B 6/00
[52] U.S. Cl. ........................... 128/653.1; 128/653.2; 128/708; 128/731; 128/733; 364/578
[58] Field of Search ................... 128/653.1, 653.2, 708, 128/731, 733; 364/578, 413.14, 413.22

Primary Examiner—Ruth S. Smith
Attorney, Agent, or Firm—Henry W. Cummings

[57] ABSTRACT

A computer system receives two dimensional slice data of a heart or other organ to be simulated in three dimensions. It also receives chemical composition data of the heart or other organ, and chemical composition data of other parts of the body. These data are put in the computer memory. Then a Voxel View or three dimensional volume rendering program forms images of the organ to be studied. For example, with the heart it generates images of the atria and ventricle. Diagnostic data obtained from a patient conveniently with electrical measurement signals including an electro-cardiagram electro-myogram, electro-encephalogram, and other diagnostic measured electrical signals obtained from a patient are fed into the system and are placed in computer memory. Physiological data of the patient, including the strength, weakness and other parameters of the organ, is also considered diagnostic data and is supplied into the system. This can be done manually with a keyboard or mouse, or may be supplied from a hard disk, a floppy disk or a tape. This is also fed into memory and is used to modify the three dimensional image data of the organ. This data is then synchronized with the electrical signal diagnostic data. Conveniently the first derivative of the electrical data signal is taken, and P and Q waves determined from the derivative. From this information the organ, including sub-parts, may be simulated. This data may be fed in black and white or preferably in color to a device which shows the organ for visualization, operation simulation, or training.

11 Claims, 4 Drawing Sheets

COMPUTER SIMULATION OF LIVE ORGAN

REFERENCE TO RELATED APPLICATION

This application is a continuation in part of application Ser. No. 07/550,343 filed Jul. 9, 1990, now abandoned.

BACKGROUND OF THE INVENTION

U.S. Pat. Nos. 3,453,745 and 3,552,036 disclose electronically operated means to simulate, control and modify ECG signals. The signals are displayed on standard osciloscope-type monitors. However, these patents only address means to simulate ECG signals.

U.S. Pat. No. 4,091,549 discloses means to trace heart electrical activity through specific points of a heart by means of illumination of specific parts of an illustration of a heart.

U.S. Pat. No. 4,254,562 discloses means to trace blood flow through specific points of a heart model or other component of a living organism.

OBJECTS OF THE INVENTION

One object of the invention is to display to an observer a pictorial image of a heart in the body of a patient generating EEG, EMG, ECG, or other diagnostic electrical signals as these signals are occurring in the patient. The diagnostic signals are commonly voltages measured of a portion of the body of the particular patient including but not limited to electroencephalogram signals measured from the brain, electrocardiogram signals measured from the heart, and electromyogram signals measured from muscle tissue of the body.

Another object is to provide a three dimensional interactive view of a heart's operation from electrical measurement signal type information.

Another object is to provide the operator with a view of an active, working heart model driven from electrical measurement signal type information in three dimensions.

Another object is to allow the operator to manipulate various characteristics and dynamics of the modelled heart or the signals from an actual or simulated EEG, EMG, ECG, or other diagnostic electrical measurement signal type monitor and observe the results on interactive, three dimensional graphical models for study, teaching, diagnosis, and research purposes.

Another object is to provide the capability to surgically or chemically interact with, probe, or explore the object of the study.

Another object is to provide the capability to do the fore-going with other parts of the body.

SUMMARY OF THE INVENTION

A computer system receives two dimensional slice data of a heart or other organ to be simulated in three dimensions. It also receives chemical composition data of the heart or other organ, and chemical composition data of other parts of the body. These data are put in the computer memory. Then a Voxel View or three dimensional volume rendering program forms images of the organ to be studied. For example, with the heart it generates images of the atria and ventricle. Diagnostic data obtained from a patient conveniently with electrical measurement signals including an electro-cardiagram electro-myogram, electro-encephalogram, and other diagnostic measured electrical signals obtained from a patient are fed into the system and are placed in computer memory. Physiological data of the patient, including the strength, weakness and other parameters of the organ, is also considered diagnostic data and is supplied into the system. This can be done manually with a keyboard or mouse, or may be supplied from a hard disk, a floppy disk or a tape. This is also fed into memory and is used to modify the three dimensional image data of the organ. This data is then synchronized with the electrical signal diagnostic data. Conveniently the first derivative of the electrical data signal is taken, and P and Q waves determined from the derivative. From this information the organ, including sub-parts, may be simulated. This data may be fed in black and white or preferably in color to a device which shows the organ for visualization, operation simulation, or training.

THE DRAWINGS

SUMMARY OF OPERATION

Figure 1:
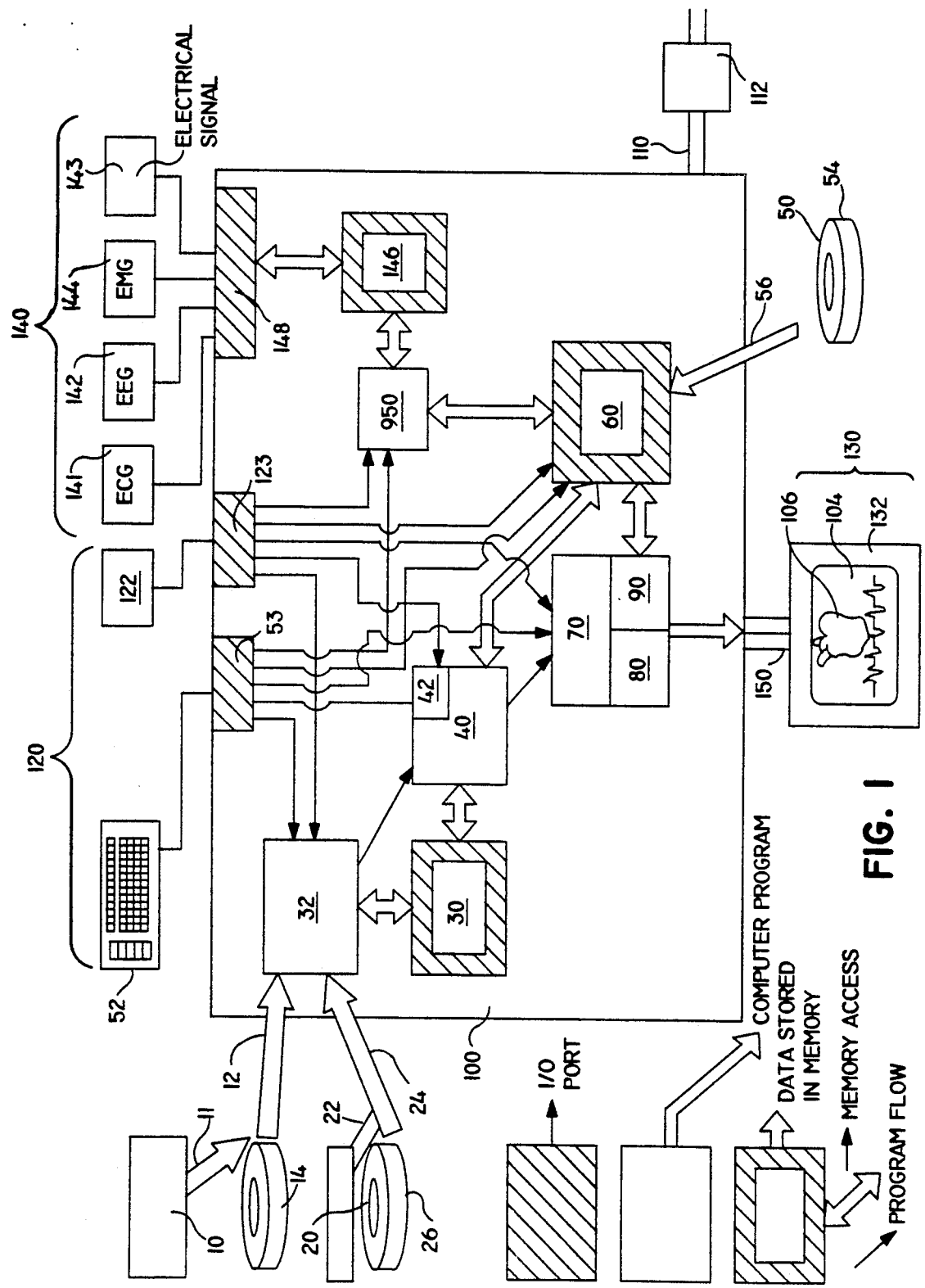
FIG. 1 is a schematic representation of the three dimensional organ monitor of the present invention.

FIG. 1 is a block diagram of the overall system. Five major features are described.

One feature is the interactive devices (120), which may be hand generated data including keyboard (52), mouse (122), touch sensitive screen, light pen, or other device. Data may also be introduced by a voice command signal.

Another feature is the input chemical composition and dimensional slice data. This may come from several sources, including Nuclear Magnetic Resonance Imaging Data (11), Computerized Tomography Data (22), or Interactive Device Generated Data, which may come from magnetic tape (14), (26), (50) or data in computer memory or from an appropriate interactive device (120).

Another feature is the diagnostic input signals (140). These may be Electrocardiogram (ECG) signals (141), Electroencephalogram (EEG), signals (142), Electromyogram (EMG) signals (144), or other diagnostic data and/or electrical input signals (143). Physiological data may be provided through communications link (56).

Another feature is the Graphics Image Generator Computer System (100). Within this computer system, which may be composed of several networked computers, several computer programs (32), (40), (70), and (950) run, accessing several blocks of memory (30), (60), and (146). These utilize the described input and output means to graphically display a three dimensional object that reflects input activity and can be manipulated by the user.

DETAILED DESCRIPTION OF PREFERRED EMBODIMENT

In accordance with the present invention, a Nuclear Magnetic resonance Scanner such as G.E. Medical Systems Model No. MR Signa Advantage 1.5 Tesla (NMRS) General Electric Co., Milwaukee, Wis., (10)

provides Imaging Data (11) in grey scale two dimensional slice format. It is used as one input to the Graphics Image Generator Computer System (100). This data is ready available and can be gathered from the patient undergoing diagnosis, or from pre-recorded data from other NMRS source. The data may enter the system via a digital data communication link (12), which enters the Graphics Image Generators Computer System (100) through a provided communications port, or read from a computer memory or magnetic tape (14). This data represents two dimensional slices of the heart or other object for study which are used to generate a three dimensional picture.

A computerized Tomography Scanner (20) such as a Siemens Medical Systems Somatom Plas supplies Scan Data (22) in grey scale two dimensional slice format is also used as input to this system. This data is readily available, and can be gathered from the patient undergoing diagnosis, or from pre-recorded data from some other CTS source. The data may enter the system via a data communications link (24) through a provided communications port, or read from a storage media, such as magnetic tape (26), hard discs and floppy discs. As an example, the chemical composition of selected parts of the body may be inputed. Other sources of chemical composition data may be used as inputs as well.

A three dimensional Volume Rendering program, (32) such as "Voxel View", which reads, CTS, NMRS, or similar data into memory (30) is activated in the Image Generator Computer System (100) to receive the data from communications links (12) and (22). "Voxel view" is a Registered Trademark of Vital Images, Inc. A brochure is in the application file, and is available from them at P.O. Box 551, Fairfield, Iowa 52556, (515) 472-7726. The data (30) is then ready to be manipulated by software (40) running in the Image Generator Computer System (100). For example, Silicon Graphics Models Nos. 4D/GTB, GTXB, or VGXB process the input data into a format suitable to the model dynamics methods. The software (40) comprises a conversion program which puts the data into a format in memory where each particular part of the heart is identified, so that model dynamics programs (950) can accurately model each part's reaction to stimulus data. The software conversion program (40) is illustrated in FIG. 2.

Figure 2:
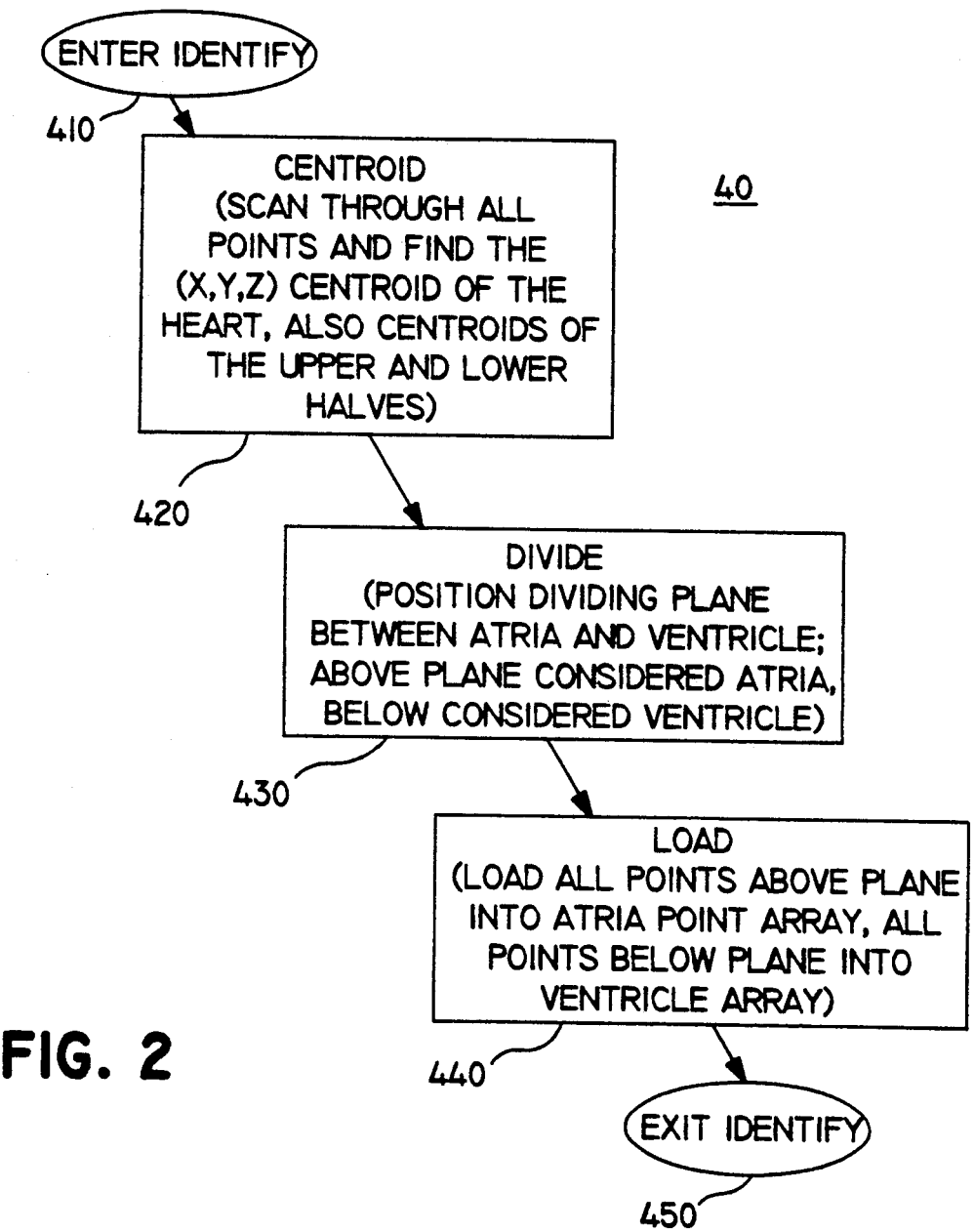
FIG. 2 is a schematic representation of the conversion model program used in the present invention.

FIG. 2 is a block diagram of an example of a simple conversion program (40) that inputs a three dimensional data block (30), and outputs two data point arrays, one for atria, and the other for ventricle points stored in memory (60). The conversion program is entered through entry point IDENTIFY (410).

First, it finds the centroid of all input data points (30) in the CENTROID section (420) of the program. It also determines the centroid of the upper and lower halves of the data. The upper and lower half centroids will be used as reference points for compressing and filling these sections.

The next section, DIVIDE (430) positions a dividing plane passing through the data centroid, dividing it into two halves. This dividing plane could be user defined. Data above the dividing plane is considered the atria and below is considered the ventricle.

The next section, LOAD (440) takes this data and transfers it to two data point arrays, one for the atria, and the other for the ventricle, in a memory section (60). The conversion program then exits (450).

Hand generated data (50) from a keyboard (52) or stored in computer memory or stored on magnetic tape (54), may be fed directly into the system by communication link (56) to add to, modify or correct slice shape data chemical composition data and to input physiological data or that data indicating the relative strength of various parts of the organ to be simulated. Data may be modified for simulation or teaching purposes through Link 56. Modified or simulated data may also be introduced through communications Link 12 and 22.

The data from the conversion program (40) and from hand generation is stored in residual memory (60) in the Graphics Image Generator Computer System (100). The image (104) of the item being studied, in this example a heart (106), is generated from this set of data. This data (60) is also accessed by the model dynamics program (950) where it is modified in the procedure shown in FIG. 3 to reflect activity in the item of study, (here heart 106).

Figure 3:
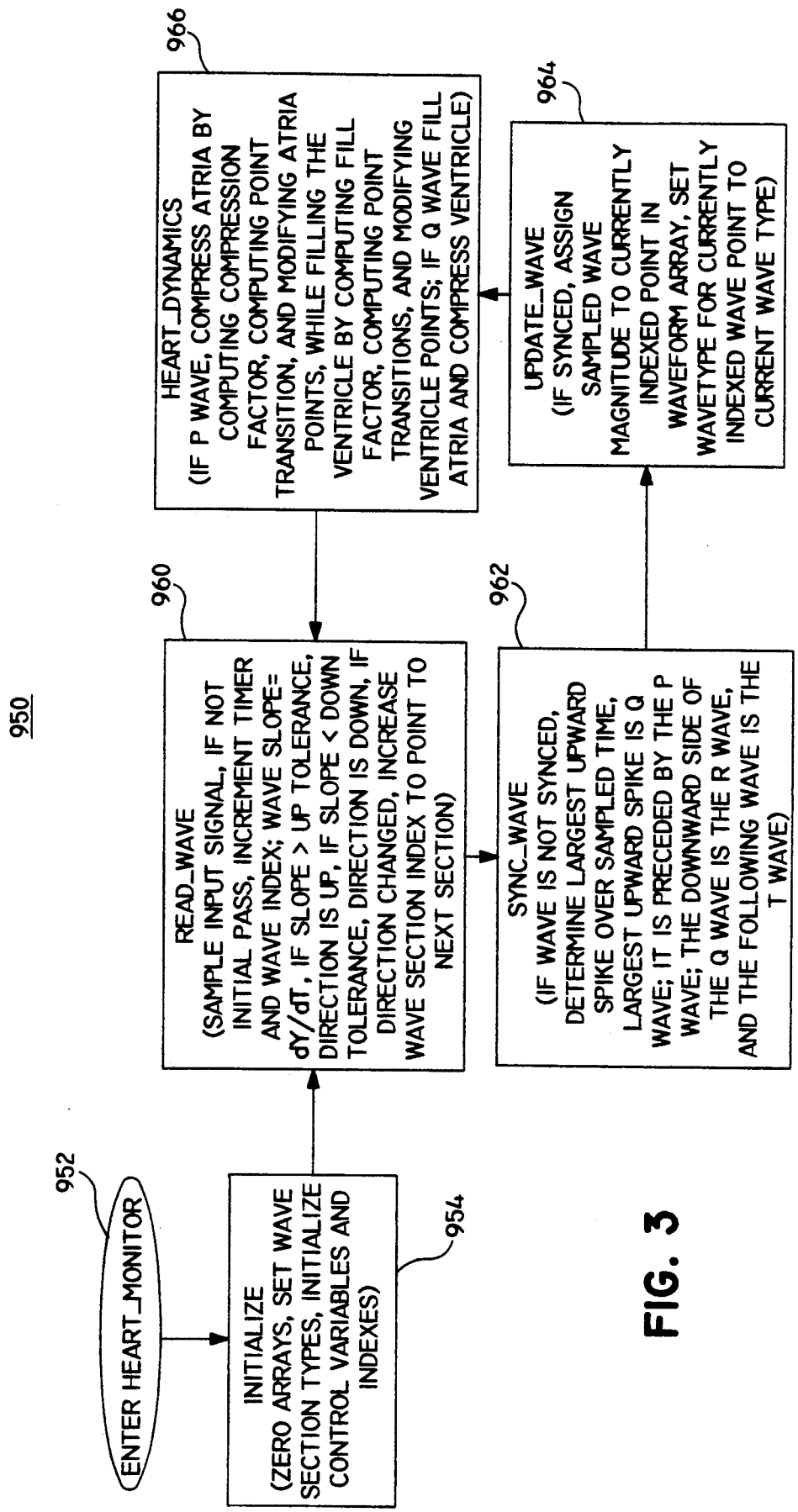
FIG. 3 is a schematic representation of the physiological model dynamics program used in the present invention.

FIG. 3 is a block diagram followed by a computer program of an example of a simple physiological model program for a dynamic heart representation (950). It is composed of an entry point (952), an initialization section (954) where memory blocks are cleared and initialized, and control variables are initialized. This program will access memory blocks (60) set up by the conversion program (40) as shown in FIG. 2.

The physiological model program then enters a loop, beginning with the Read-Wave section (960) where input signals data is accessed from memory 146. The first derivative of the input signal magnitude with respect to time will indicate whether the signal is increasing or decreasing. With each change of direction, an index identifying the current wave section is incremented. This index identifying the current wave section must be synchronized with the actual input signal, and this synchronization is done in the next section, sync-wave (962).

A flat is set when the wave is known to be synchronized and that section is skipped. Otherwise, the section samples the input signal over a period of time. The largest upward spike is the Q wave, where the wave magnitude corresponds to ventricle compression. When synchronized, the sync flag is set, and this section will not perform again unless synchronization is lost.

The next section is the update-wave section (964). It is performed if the input signal and physiological model program are known to be synchronized (i.e., the sync flag is set). This section accesses the wave section index set in the read-wave section (960). It also accesses the current input signal (148), and assigns this magnitude to the currently indexed point in a memory section known as the wave form array. It also sets the wave type for the currently indexed point in the wave form array to the current wave type using the current wave section index set in the read-wave section (960).

The next section is the Heart-Dynamics Section (966). It accesses the memory (60) where the arrays describing the three dimensional locations of points on the surface of specific contours of the heart is stored. If the currently indexed point has a "P" wave type, the atria is compressed, and the ventricle is filled. A "Q" wave type will fill the atria, and compress the ventricle. Compression of points is done by computing a compression factor, dependent upon the magnitude of the input signal, computing three dimensional point transition using the compression factor, and modifying the array points containing the three dimensional location of the points of the section to be compressed. The same process is done when filling a section, the difference being, a fill factor is used instead of a compression factor. After the heart-dynamics section (966), the physiological model program returns to the read-wave section (960), where the current input signal is again sampled, the direction of signal change is noted, and the loop is repeated.

A Three Dimensional Graphics Program (70), that accesses the data (60) is provided which uses geometric image functions (80) provided by Graphics Image Generator Computer System (100) to draw an image of the item of study, and reflects the activity of the item, such as a heart, as modelled by the model dynamics program (950). Geometric Image Functions (80), are provided to draw simple shapes or objects. Program (70) uses these functions to produce an image of the item of study such as heart (106). The Three Dimensional Graphics Program (70) is illustrated in FIG. 4.

Figure 4:
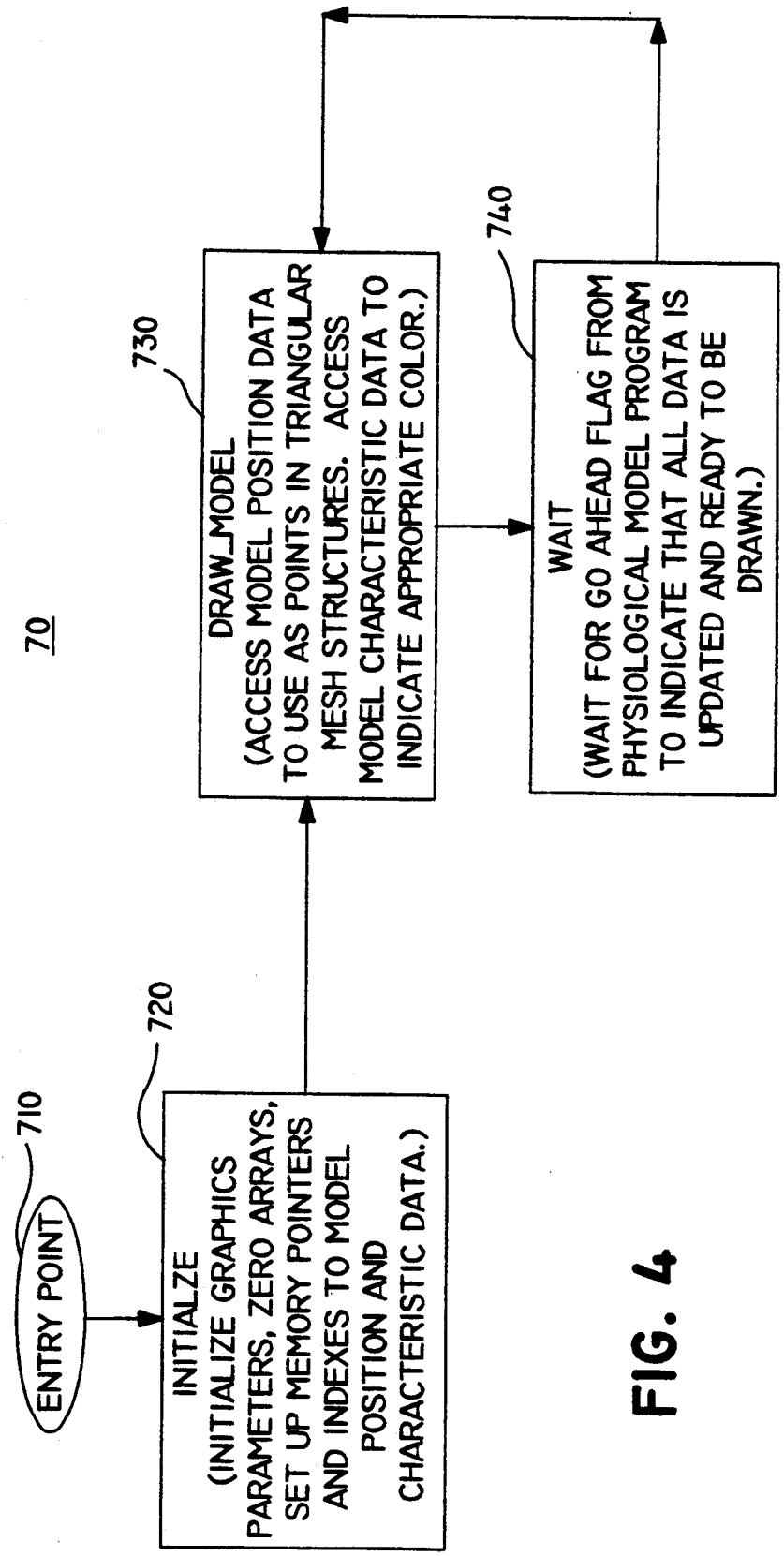
FIG. 4 is a schematic representation of the three dimensional graphics program used in the present invention.

FIG. 4 is a block diagram of the three dimensional graphics program (70). It runs in parallel with the physiological model programs (950) to draw an image of the item of study, in this embodiment a heart.

The program is entered through entry point 3DMODEL (710), and continues into the initialization section (720) where control variables are set up. The program then proceedes to the DRAW_ MODEL (730) section, where graphics image functions are accessed to draw the model using simple geometric shapes. In this example, a triangular mesh technique is appropriate, and is fully documented by Silicon Graphics, makers of the preferred embodiment Graphics Image Generator Computer. When the update pass through the graphics image functions is completed, the program waits (740) for the physiological model programs (950) to signal the 3D Graphics Program (70) to update the display. It then repeats the DRAW_ MODEL section (730) and continues looping.

The Machine Operating System (90) runs within the Graphics Image Generator Computer (100) and is the interface between the user and the Graphics Generator Machine. The preferred operating system is IRIX, which is well known, and information is available in publications concerning the Graphics Image Generator. For example, see the IRIX System Library, available from Silicon Graphics.

The preferred embodiment Graphics Image Generator is then IRIS 4D/3220VGXB from Silicon Graphics of Shoreline Blvd., P.O. Box 7311, Mountain View, Calif. 94037-2011. It has a one million vectors/second and one million polygons/second capacity. Publications are available concerning the use of this system and are found in the IRIS System Library, available from Silicon Graphics. In the preferred embodiment it is equipped with analog input capacity, into which external signals such as ECG (141), EEG (142), EMG (144), or other electrical signals (143) are input.

In the preferred embodiment Graphics Image Generator System, the preferred Graphics Image Generator Computer is the IRIS 4D/320VGXB, and all computer programs are executed within it, but the Graphics Image Generator Computer System may consist of several computers linked or networked together.

Power for the system is 120 volt house current (110) preferably having surge protection (112) included, is also provided.

Interactive Devices (120) such as a keyboard (52) and mouse (122) are supplied with the Graphics Image Generator Computer (100). The preferred devices are a silicon graphics keyboard, model number EO 3410051, part number 30097 and a silicon graphics mouse, model number M4. The keyboard (52) connects to the keyboard port (53), and the mouse (122) connects to the mouse port (123) provided with the Graphics Image Generator Computer (100). These interactive devices (120) interact with all software program (32), (40), (70), and (950) running in the system.

The image of the item of study is displayed on an output device (130). In the preferred embodiment a Color CRT Terminal (132) such as a Mitsubishi Color Display Model No. HA 3905, AC120 v, 60 Hz, 1.6A is used.

Input signals (140) from an electrocardiogram (ECG 141), electroencephalogram (EEG 42), electromyogram (EMG 144) and/or other electrical input signals (143) are supplied to an analog input (148) into computer memory (146) of the Graphics Image Generator (100). These inputs may be direct output from an actual ECG (141), EEG (142), EMG (144), an ECG, EEG, or EMG simulator or other electrical input signals (143). These are well known diagnostic devices, and techniques for generating simulated signals thereof are also well known.

Standard Red-Green-Blue (RGB) connectors (150) are used in the preferred version to connect the CRT terminal (132) to the Graphics Image Generator Computer System (100). These connectors are supplied with the CRT (132) and are conventional.

The Input Data, such as ECG (141), EEG (142), EMG (144), or other electrical input signals (143) is converted in the Graphics Image Generator (100) to digital form at a memory location (146) for use in the model dynamics program (950) by analog input (148).

The Model Dynamics Program (950), such as those for modelling a heart, use either actual or simulated input signals such as ECG (141), EEG (142), EMG (144), or other electrical input signals (143) to determine the reaction of the item of study. It accesses the data (60) for modification to reflect the input signal dynamics, and the updated data is then displayed in the image (104) via the three dimensional graphics program (70) accessing the shared image data in memory (60).

The system described herein consists of input data from various sources including, but not limited to, NMR data (10), CT data (20), hand generated data (50), or other diagnostic data. Also included are appropriate interactive devices (120), such as a keyboard (52), mouse (122), or other devices such as touch sensitive screens, light pens, voice recognition systems, or other compatible interactive means (not shown).

The Graphics Image Generator Computer System (100) is where the software programs run, and input data is stored and manipulated in its memory. The Graphics Image Generator Computer System may consist of several interconnected computers. The software programs, such as Volume Rendering type (32), input conversion (40), three dimensional graphics (70), and physiological model (950), are user activated via appropriate devices, including keyboard (52) or mouse (122). The user first activates the Volume Rendering type input program (32) to bring the NMR (10), CT (20) or other data source into a computer memory block (30). The user then activates the input data conversion program (40), which accesses the Volume Rendering type program output data (30), puts it into a manipulatible form in memory (60) for the physiological model programs (950) and three dimensional graphics programs (70) to access.

After the conversion program (40) is completed, the user activates the three dimensional graphics program (70), which accesses the converted data in memory (60), and generates the image (104), in this case a heart (106). The three dimensional graphics program (70) continually loops within itself, accessing the data in memory (60) and updating the display (130) each pass through until the user interrupts the task. While the Three Dimensional Graphics Program (70) is running, the physiological model program (950) is activated to monitor the input signals (140), and modify the data in memory (60) to reflect the input signals.

Meanwhile, the three dimensional graphics program (70) is accessing the memory (60) as updated by the physiological model program (950) and the resultant change is seen in the display (130).

In this case, the programs (70) and (950) are running in parallel in separate processors to take advantage of the dual processors in the preferred embodiment Graphics Image Generator Computer System (100), the IRIS 4D/320VGXB. In accordance with the present invention, the programs could be further parallelized by using more processors, or may run sequentially if only one processor is available. Information on parallelization is available in the Silicon Graphics' Publications Library, available from Silicon Graphics. Other processors may be added by interconnecting the system with other computers to increase processing power, or processors may be replaced as faster ones become available.

The programs and parameters used in these models may be modified or updated depending on the intent of the study or diagnoses, and may model a wide variety of body functions including muscles and nerve signals throughout the body or bodies. Any object with three dimensional data and knowledge of its properties available may be modelled by this system.

What is claimed is:

1. An organ image generating computer system comprising:
    means for obtaining nuclear magnetic resonance imaging data directly from a patient;
    means for obtaining patient chemical composition tomography scan data directly from a patient;
    means for detecting electrical diagnostic data from a patient;
    a computer system including means for inputting said imaging data, said scan data and said diagnostic data into a three dimensional volume rendering program;
    means for processing said inputted data within said computer system to form an organ image and any movement of said organ; and
    means for transmitting said organ image to a display device where said organ image and any movement of said organ is displayed.

2. An organ image generating system according to claim 1 wherein said means for detecting electrical diagnostic data includes means for detecting electrocardiogram data.

3. An organ image generating system according to claim 1 wherein said means for detecting electrical diagnostic data includes means for detecting electromyogram data.

4. An organ image generating system according to claim 1 wherein said means for detecting electrical diagnostic data includes means for detecting electroencephalogram data.

5. A system according to claim 1 wherein said display device is a Cathode Ray Tube (CRT).

6. A method of modelling an animal organ comprising:
    providing an image generator computer system;
    supplying to said computer system image data from a nuclear magnetic resonance imaging machine;
    supplying to said computer system chemical composition computerized tomography scan data;
    supplying electrical diagnostic data from a patient to said computer system;
    processing said image data and scan data in said computer system with a volume rendering computer program to form a three dimensional image;
    processing said diagnostic data in said computer system with said three dimensional image to form an organ image and any movement of said organ;
    transmitting said organ image to a display device; and
    displaying said organ image and any movement thereof in said display device.

7. An organ computer simulation system comprising:
    a computer having a computer memory;
    electrode means for obtaining at least one diagnostic data waveform from a patient;
    diagnostic data waveform input means for supplying said diagnostic data waveform into said computer;
    means for obtaining organ cross sectional slice data from a patient;
    slice data input means for supplying said organ slice data into said computer;
    means for obtaining chemical composition data from said patient;
    input means for supplying said chemical composition data into said computer;
    computer processing means in said computer for processing said diagnostic data, said slice data, said chemical composition data to define an organ sub-part waveform;
    means for calculating any organ movement of said organ as a result of changes in said sub-part waveform;
    and means for displaying said organ and any movement thereof resulting from changes in said sub-part waveform.

8. An organ simulation system comprising:
    a computer having a computer memory;
    electrode means for obtaining diagnostic data from a patient having an organ to be simulated;
    diagnostic data electrical input means for supplying said diagnostic data into said computer memory;
    imaging means for obtaining cross sectional slice data from said patient;
    slice data electrical input means for supplying said slice data to said computer memory;
    chemical composition electrical input means for supplying chemical composition data relative to said patient into said memory;
    means for accessing said diagnostic data, said slice data and said chemical composition data from said computer memory;
    means for transferring said diagnostic data, slice data, and chemical composition data to a computer processor;
    processing means in said computer for taking the first derivative of said diagnostic data with respect to time to define a diagnostic waveform;
    means for synchronizing said diagnostic waveform with said slice data and chemical composition data to define a combination wave for illustrating of said organ;

means within said computer for calculating movement of said organ based upon changes in said combination wave; and means for displaying in color said organ and any movement thereof based on changes in said combination wave for observation.

9. A heat computer simulation system comprising:

a computer having a computer memory;

electrode means for obtaining at least one diagnostic data wave form from a patient;

said computer memory including diagnostic memory means for storing said diagnostic data wave form within said memory;

imaging means for obtaining cross sectional slice data from a patient;

slice data input means for supplying said slice data to said computer memory;

chemical composition electrical input means for supplying chemical composition data relative to said patient into said memory;

said memory including means for storing said slice data and said chemical composition data within said system;

accessing means for accessing said slice data and said chemical composition data from said memory;

transferring means for transferring said slice data and said chemical composition data to at least one image generating computer processor;

said image generating processor processing said slice and chemical composition data to define heart subpart atria and ventricle three dimensional data;

means for transferring said three dimensional data to a physiological model processor;

means for processing said three dimensional data in said physiological model processor in a loop;

means for accessing said diagnostic data waveform from said diagnostic data memory means;

means for transferring said diagnostic data wave form to said physiological model processor and into said loop;

means for taking the first derivative of said diagnostic data waveform with respect to time to obtain the direction and rate of change of a diagnostic data waveform in said loop;

manual means for modifying one of said chemical composition data, and slice data as a result of the direction and rate of change of said diagnostic data waveform;

means for synchronizing said diagnostic data waveform and said three dimensional data to define P and Q wave waveform signals;

means for computing a compression factor based on said P wave and said Q wave signals, said P wave compressing the atria and filling the ventricle, and the Q wave filling the atria and compressing the ventricle;

graphic image means for continuously simulating the heart and any movement thereof as a result of said modification of said slice, and chemical composition data; and cathode ray tube means for displaying said heart and any movement thereof in color for observation.

10. A method of simulating an organ in a computer system comprising:

obtaining diagnostic data from a patient with electrical contacts attached to said patient;

forming an image from cross-sectional slice data of the patient's organ;

supplying said slice data to a computer simulation system;

transferring said slice data to an image generator computer processor in said computer simulation system;

processing said slice data within said image generator computer processor to define said patient's organ data;

supplying said organ data to a physiological model processor within said computer simulation system;

supplying said diagnostic data to said physiological model processor to obtain a diagnostic data waveform;

synchronizing said diagnostic data waveform with said organ data, within said processor;

processing said organ data and diagnostic data waveform to obtain a synchronized wave;

drawing the organ, with a graphic image system based on said synchronized wave;

transferring the drawn image to a display device; and displaying any movement of the organ based on said synchronized wave for observation in said display device.

11. A method of simulating an organ in a computer system comprising:

obtaining diagnostic data from a patient with electrical contacts attached to said patient;

obtaining chemical composition data relative to the patient;

supplying said chemical composition data to a computer simulation system;

forming an image from cross sectional slice data of the patient's organ;

supplying said slice data to said computer simulation system;

transferring said slice data and chemical composition data to an image generator computer processor in said computer simulator system;

processing said chemical composition data and said slice data within said image generator computer processor to define said patient's organ data;

supplying said organ data to a physiological model processor within said computer simulation system;

supplying said diagnostic data to said physiological model processor to obtain a diagnostic data waveform;

synchronizing said diagnostic data waveform with said organ data, within said processor;

processing said organ data and diagnostic data waveform to obtain a synchronized wave;

drawing the organ, with a graphic image system based on said synchronized wave;

transferring the drawn image to a display device; and displaying any movement of the organ based on said synchronized wave for observation in said display device.

* * * * *